United States Patent [19]

Khanna et al.

[11] Patent Number: 4,975,248

[45] Date of Patent: Dec. 4, 1990

[54] KIT FOR OBTAINING A DIGOXIN CONCENTRATE FROM A SERUM SAMPLE

[75] Inventors: Pyare Khanna, San Jose; Roberta D. Ernst, Sunnyvale; Anne J. Stone, Los Altos, all of Calif.

[73] Assignee: Syntex (U.S.A.) Inc., Palo Alto, Calif.

[21] Appl. No.: 919,404

[22] Filed: Oct. 16, 1986

Related U.S. Application Data

[62] Division of Ser. No. 621,301, Jun. 15, 1984, Pat. No. 4,654,311.

[51] Int. Cl.$^5$ .............................................. G01D 1/28
[52] U.S. Cl. .................................... 422/61; 210/282; 210/656; 422/70; 436/14; 436/161; 436/178
[58] Field of Search ............... 422/61, 69, 70; 436/94, 436/161, 174, 175, 177, 178; 210/282, 656

[56] References Cited

U.S. PATENT DOCUMENTS

| | | | |
|---|---|---|---|
| 4,131,544 | 12/1978 | Elahi | 422/69 X |
| 4,409,335 | 10/1983 | Hanamoto et al. | 422/61 X |
| 4,476,093 | 10/1984 | Watanabe et al. | 422/61 |

FOREIGN PATENT DOCUMENTS

| | | | |
|---|---|---|---|
| 2605789 | 8/1976 | Fed. Rep. of Germany | 210/656 |
| 857860 | 8/1981 | U.S.S.R. | 436/161 |
| 2074042 | 10/1981 | United Kingdom | 210/656 |

OTHER PUBLICATIONS

Issaq et al., J. Liquid Chromatography, vol. 5, No. 6, pp. 1069–1080, (1982).

Issaq et al., Chemical Abstracts, vol. 97, Abstract No. 97:49014z, 1982.

Berendsen et al., J. of Chromatography, vol. 196, pp. 21–37, 1981.

Kabra et al., "Clinical Liquid Chromatography", vol. I-Analysis of Exogenous Compounds, CRC Press, 1984, 197–208.

*Primary Examiner*—Robert J. Hill, Jr.
*Attorney, Agent, or Firm*—Theodore J. Leitereg

[57] ABSTRACT

Serum is passed through a column containing silica gel alkylated with lower alkyl groups. The column is then washed with dilute acid and water and the digoxin eluted with aqueous methanol at a volume less than about the volume of the serum to provide a digoxin concentrate that may be used in assay determinations. The invention also includes a kit comprising in a packaged combination for use in an assay for digoxin (a) a column containing silica gel alkylated with alkyl groups containing 1 to 2 carbon atoms and (b) an aqueous eluent solution which is 50%–70% by volume organic solvent. The organic solvent comprises from 1–4 carbon atoms and from 1–3 heteroatoms selected from the group consisting of oxygen and nitrogen.

7 Claims, No Drawings

KIT FOR OBTAINING A DIGOXIN CONCENTRATE FROM A SERUM SAMPLE

This is a division of pending application Ser. No. 621,301, filed June 15, 1984, now U.S. Pat. No. 4,654,311 incorporated herein by reference.

BACKGROUND OF THE INVENTION

Field of the Invention

Digoxin, and derivatives of digoxin, find wide use in cardiac treatment, frequently as a component of digitalis. Digoxin is highly potent in its activity and has a narrow therapeutic range In addition, the drug can produce serious side effects so that monitoring the digoxin level in blood is important for the well-being of the patient Since the therapeutic range is from about 0.8 to 2.0 ng/ml, it is necessary not only to measure extremely small amounts of digoxin in serum, but also to be able to distinguish between small differences in concentrations Depending upon the sensitivity of the assay, the digoxin concentration in serum may be insufficient for detection when diluted into the assay medium. Also, naturally occurring materials in the serum sample may modify the observed signal so as to give false results. It would therefore be desirable to provide for a simple means for tretreatment of a serum sample for a digoxin assay. The pretreatment method should be rapid and efficient and provide an assay sample containing the drug in a concentrated amount free of interfering substances.

DESCRIPTION OF THE PRIOR ART

A radioimmunoassay for determining the digoxin content of a sample is disclosed in U.S. Pat. No 3,981,982 An enzyme amplification assay is described in U.S. Pat. No. 3,817,837.

SUMMARY OF THE INVENTION

Serum samples for digoxin assays are pretreated by passing the serum sample through a column usually a pre-prepared column, containing silica gel that is alkylated with lower alkyl groups. The column is then washed with dilute acid and water, and the digoxin is eluted with aqueous methanol to provide a concentrated Sample of digoxin free of interfering substances. The pretreatment method finds particular application in conjunction with assays employing enzyme or fluorescent labels.

DESCRIPTION OF THE SPECIFIC EMBODIMENTS

Serum samples for digoxin assays are pretreated to provide for at least about a two-fold concentration of digoxin in a medium substantially free of materials present in the serum sample and in a form useful for a digoxin assay determination. It is believed that the present method allows separation of digoxin from endogenous proteins present in serum samples to which proteins the digoxin is bound. The method normally employs reverse phase liquid chromatography using a column containing silica gel alkylated wit h alkyl groups of from 1-2 carbon atoms, particularly 1 or 2 carbon atoms. The silica gel particles have a size in the range of about 30-50 $\mu$m, preferably about 40 $\mu$m. The particles are silanized with methyl or ethyl silyl groups to provide the alkylated silica gel particles The amount of the column packing, i.e., alkylated silica gel, employed and the dimensions of the column are dependent on the size of the serum sample to be treated. Generally, for a serum sample of one ml, about 50 to 100 mg of packing will be used. For 50 mg of silica gel depending upon the manner of packing, as well as the diameter of the column, the height of the column may vary from about 7 to 20 mm.

The column is packed by introducing the silica gel powder into an appropriate column The column is pre-prepared, i.e. conditioned, by adding methanol followed by water and removing the solvent by any convenient means, e.g., vacuum, positive pressure centrifugation, or the like. After the methanol has been removed, the column is then washed with water, preferably deionized water. The water is then removed as described above, and the column is now ready for the sample.

Prior to applying the sample to the column, the serum sample may be subjected to other pretreatments depending upon the nature of the sample, such as icteric, lipemic, uremic, or the like, the sample may be centrifuged, subjected to chromatographic treatment, filtration, or the like.

The sample is then added to the column after all the excess methanol and water employed in the pretreatment and washing of the column have been removed. The sample may then be drawn into the column by vacuum or centrifugation, or it may be pushed into the column by positive pressure. The conditions for putting the sample on the column will be generally mild, for example, a vacuum in the range of about 10-20 inches Mg may be used. Various conventional devices can be used, for example, the Vac-Elut® vacuum box (Analytichem International).

After the sample has been put onto the column, the column is be washed with a small amount of 0.05-0.2N HCl, more usually about 0.1N HCl. The volume of the acid wash is not critical, usually being about one times the column volume, generally less than about 5 ml, more usually less than about 2 ml and usually at least about 1 ml. After the acid wash, the column is then washed with deionized water to ensure the removal of any remaining materials that are not adsorbed onto the column packing material Again, the amount of water which is used is not critical, usually being about one times the column volume, generally being less than about 10 ml, more usually being less than about 5 ml, and preferably at least about 1 ml. After each addition of the wash solution, the wash solution may be drawn through the column as described above for the sample. Usually this will involve, for an initial volume of 1 ml sample, at least about 15 seconds and not more than about two minutes, generally from about 20 seconds to 45 seconds Any water remaining at the tip of the column may be removed by blotting or other convenient means.

The digoxin is then eluted to provide for a digoxin concentrate in purified form to be used in an assay. Elution is accomplished by adding at least about 150 $\mu$l, preferably at least about 250 $\mu$l, and preferably, not more than about 500 $\mu$l of eluent for an initial volume of 1 ml of serum sample. The lower the eluent volume, the greater the concentration of digoxin will be in the final sample. The eluent is generally an aqueous organic solvent wherein the organic solvent generally comprises from 0 to 4 carbon atoms and from 1 to 3 heteroatoms selected from the group consisting of oxygen and nitrogen. Exemplary of such an eluent is 50% aqueous methanol up to 100% methanol, preferably about 60% aqueous methanol. Other organic solvents that may be employed are dimethyl formamide, ethanol, etc. In assays involving labels, e.g., enzyme labels, the organic solvent should have little or no detrimental effect on the label activity. In that respect, consideration should also be given to techniques for combining the digoxin concentrate with the assay reagents as this may effect label activity. The aqueous methanol is drawn through the column in the same manner described above The aqueous methanol may be added to the column in 200-500 μl aliquots, the eluate being drawn through the column before the next addition. Usually, about 1-3 aliquots, preferably one aliquot, of the aqueous methanol is employed to give an assay sample volume of less than about 50%, usually about 30-50%, of the initial serum sample volume. The eluate is then collected and is ready to be used in an assay.

Serum samples treated to give digoxin concentrates in accordance with the present invention may be assayed for digoxin by a number of assay methodologies. The assays may be heterogeneous or homogeneous involving labels such as enzymes, radioisotopes, fluorescers, and the like. The method of the invention is particularly suited for preparing digoxin concentrates for enzyme label assays such as, for example, EMIT ® assays, EMIT ® QST ™ assays, etc.

The invention also includes a kit comprising, in a packaged combination, (1) a prepacked column having dimensions as described above and containing silica gel, alkylated with alkyl groups containing from 1 to 2 carbon atoms in amounts as described above, to which column the serum sample is to be applied, and (2) about 300 μl 500μl of 50-70% aqueous organic solvent, which organic solvent comprises from 1 to 4 carbon atoms and from 1 to 3 heteroatoms selected from the group consisting of oxygen and nitrogen, such as methanol, as an eluent in a suitable container such as a vial made of a suitable material such as glass or plastic The kit may also include ancillary items such as a device for securing the serum sample or applying the serum sample to the column, wash solutions such as a dilute aqueous mineral acid, e.g., HCl, in amounts and concentrations as described above, deionized water, etc. in separate containers and so forth The above kit may be combined with an assay kit for performing a digoxin assay or it may be separate therefrom.

As used herein above the term "percent (%) aqueous organic solvent " means volume percent of organic solvent in the aqueous medium.

EXAMPLE

The invention is further demonstrated by the following illustrative example, which is provided by way of illustration and not limitation.

A Vac-Elut ® vacuum box (Analytichem International) was used at 12-15 inches Mg. Up to ten columns (C-2 from Analytichem containing silica gel alkylated with methyl groups) were placed in luer fittings in the lid of the vacuum box and any remaining holes were plugged with stoppers Each of the columns was filled with spectral grade methanol and the methanol drawn through with a vacuum of 13 inches Mg. The column was then rinsed with one column-volume of deionized water to displace the methanol. Onto each column was accurately pipetted 1.0 ml of a serum sample and the sample drawn through with a vacuum of 13 inches Mg. The column was rinsed with one column-volume of 0.1M HCl to remove any extraneous substances The column was rinsed with one column-volume of deionized water to wash off any remaining materials not adsorbed to the column packing material. Vacuum was applied until no water was left on the column, approximately 30 seconds (A column-volume equals 1-2 ml ) Any water remaining on the column outlets was removed by blotting A metal collection rack with 10×75 mm test tubes was placed in the vacuum box to collect the eluates Using an Oxford dispenser, either 500 μl of 60% methanol was added to each column or 300 μl in two 150 μl aliquots. The eluent was 60% methanol and was drawn through the column by means of vacuum. The collection tubes were capped and stored until used.

In the first study, a number of assays were performed on a Cobas Bio instrument (available from Hoffman-LaRoche Corporation, New Jersey) according to the operating instructions provided by the manufacturer for conducting an EMIT ® assay. The parameters for the assay are as follows:

| | | |
|---|---|---|
| 1. | Units | ng/ml (enter "13") |
| 2. | Calculation factor | 8,000 |
| 3a. | Standard 1 Conc. | 0.0 |
| b. | Standard 2 Conc. | 0.5 |
| c. | Standard 3 Conc. | 1.0 Enter Calibrator Concs. |
| d. | Standard 4 Conc. | 2.0 |
| e. | Standard 5 Conc. | 3.5 |
| f. | Standard 6 Conc. | 5.0 |
| 6. | Limit | 0 |
| 7. | Temperature (Deg. C.) | 37.0 |
| 8. | Type of Analysis | 7.3 |
| 9. | Wavelength (nm) | 340 |
| 10. | Sample volume (μl) | 24 |
| 11. | Diluent volume (μl) | 15 |
| 12. | Reagent volume (μl) | 135 |
| 13. | Incubation time (sec.) | 10 |
| 14. | Start reagent volume (μl) | 70 |
| 15. | Time of first reading (sec.) | 1.0 |
| 16. | Time interval | 120 |
| 17. | Number of readings | 5 |
| 18. | Blanking mode | 0 |
| 19. | Printout mode | 1 Enter Curve Model |

The protocol employed the following reagents:
1. Reagent A: 1 to 3500 dilution of neat digoxin antibody with 2 × substrate
2. Reagent B:
1 to 220 dilution of neat digoxin-glucose-6-phosphate dehydrogenase (G6PDH) conjugate in B diluent. (B diluent composition is as follows:)
0 05M Tris HCl
0.45% NaCl
0.05 NaN$_3$
1% RSA
pM 7.6
Assay Buffer:
0.6% NaCl
0.132M Tris
0 006% Thimerosal
0 12% Triton X-100
0.06% NaN$_3$
pH = 8.4
4. Working Reagent A:
Prepared by combining one volume of Reagent A with 8 volumes of Assay Buffer.

5. Working Reagent B:
Prepared by combining 3 volumes of Reagent B with 11 volumes of Assay Buffer.

6. Calibrators:
Freon treated serum was used as a matrix for the calibrators.

7. Calibrator Levels:

| Calibrator # | Nominal Digoxin Conc. (ng/ml) |
|---|---|
| 0 | 0.0 |
| 1 | 0.5 |
| 2 | 1.0 |
| 3 | 2.0 |
| 4 | 3.5 |
| 5 | 5.0 |

8. Calibrators were subjected to a column extraction procedure which was the same as that described above for the serum samples to be assayed.

The recovery of digoxin from the 100 mg columns was evaluated with spiked levels of digoxin at 0.7 ng/ml and 3.5 ng/ml The digoxin was spiked into a pool of digoxin negative sera. For ten samples at 0.7 ng/ml, the mean value was 0.691 ng/ml, standard deviation (SD) was 0.06, percent coefficient of variation (CV) was B.7, and percent recovery was 98 5%. At the 3.5 ng/ml, the comparable results were 3.46, 0.15, 4.3 % and 98.9.

The procedure was repeated In back-to-back comparisons conducted as described above, the Analytichem 100 mg C1 column with a 60% methanol eluent was compared with Analytichem 100 mg C2 column (contained silica gel alkylated with ethyl groups) with 70% methanol as the eluent. The results are reported as the observed change in signal as compared to a sample having no digoxin. The following table indicates the results.

| Digoxin (ng/ml) | $\Delta A^* - \Delta A_o^{**}$ | |
|---|---|---|
| | C1 | C2 |
| 0.0 | — | — |
| 0.5 | 36 | 27 |
| 1.0 | 57 | 56 |
| 2.0 | 89 | 84 |
| 3.5 | 124 | 122 |
| 5.0 | 139 | 130 |

*$\Delta A$ is the rate for a sample containing the stated digoxin concentration.
**$\Delta A_o$ is the rate for a sample containing no digoxin.

The results are comparable except that a better spread seems to be obtained with the C1 column than with the C2 column In the next study, results were compared using digoxin samples prepared in accordance with the subject invention in an assay as described above and a radioimmunoassay on unextracted samples. The RIA assay was purchased from Clinical Assays, Cambridge Mass. (GammaCoat TM [$^{125}$I ] Digoxin Radioimmunoassay Kit). The RIA was performed in accordance with the supplier's instructions A statistical summary of the results follow:

| | | | |
|---|---|---|---|
| Slope: | 1.086 | Intercept: | −.339 |
| SE slope: | .024 | SE intercept: | .051 |
| $X_{avg}$: | 2.001 | $Y_{avg}$: | 1.834 |
| $SD_x$: | .834 | $SD_y$: | .901 |
| Correlation: | .945 | SEE: | .204 |
| N: | 108 | | | wherein
x=RIA performed in accordance with the supplier's instructions.
y=EMIT ® assay performed in accordance with the present invention
avg=average
SE=standard error
SD=standard deviation
SEE=standard error of the estimate
N=number of samples It is evident from the above results that the subject method greatly enhances the accuracy and reproducibility of digoxin assays, particularly involving enzyme labels. Thus, a sensitive and efficient method is provided for treating samples for digoxin assays which results in accurate determinations of digoxin.

Although the foregoing invention has been described in some detail by way of illustration and example for purposes of clarity of understanding, it will be obvious that certain changes and modifications may be practiced within the scope of the appended claims

What is claimed is:

1. A kit for purifying a serum sample to give a digoxin concentrate for use in an assay for digoxin, which kit comprises:
    (a) a column containing silica gel alkylated with alkyl groups containing 1-2 carbon atoms.
    (b) an aqueous eluent solution which is 50-70% by volume organic solvent, which organic solvent comprises from 1 to 4 carbon atoms and from 1 to 3 heteroatoms selected from the group consisting of oxygen and nitrogen, and
    (c) a dilute aqueous acid in a separate container.

2. The kit of claim 1 wherein said acid is a mineral acid.

3. The kit of claim 1 wherein said organic solvent is methanol.

4. The kit of claim 1 wherein said silica gel is methanol-washed silica gel.

5. A kit for purifying a serum sample to give a digoxin concentrate for use in an assay for digoxin, which kit comprises:
    (a) a column containing silica gel alkylated with alkyl groups containing 1-2 atoms,
    (b) an aqueous eluent solution which is 50-70% by volume organic solvent, which organic solvent comprises from 1 to 4 carbon atoms and from 1 to 3 heteroatoms selected from the group consisting of oxygen and nitrogen, and
    (c) deionized water in a separate container.

6. The kit of claim 5 wherein said organic solvent is methanol.

7. The kit of claim 5 wherein said silica gel is methanol-washed silica gel.

* * * * *